(12) United States Patent
Nozato et al.

(10) Patent No.: US 9,277,858 B2
(45) Date of Patent: Mar. 8, 2016

(54) ABERRATION CORRECTING METHOD AND ABERRATION CORRECTING APPARATUS

(71) Applicant: CANON KABUSHIKI KAISHA, Tokyo (JP)

(72) Inventors: Koji Nozato, Rochester, NY (US); Kohei Takeno, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/133,364

(22) Filed: Dec. 18, 2013

(65) Prior Publication Data

US 2014/0176907 A1    Jun. 26, 2014

(30) Foreign Application Priority Data

Dec. 21, 2012   (JP) .................................. 2012-279478

(51) Int. Cl.
*A61B 3/14*   (2006.01)
*A61B 3/10*   (2006.01)
*A61B 3/12*   (2006.01)

(52) U.S. Cl.
CPC ............... *A61B 3/102* (2013.01); *A61B 3/1015* (2013.01); *A61B 3/12* (2013.01); *A61B 3/14* (2013.01)

(58) Field of Classification Search
CPC .................................... A61B 3/14; A61B 3/12
USPC .................................. 351/200, 205, 206, 246
See application file for complete search history.

(56) References Cited

U.S. PATENT DOCUMENTS

2012/0019780 A1*   1/2012   Nozato ........................ 351/221
2013/0321767 A1*   12/2013  Hirose ........................ 351/206

OTHER PUBLICATIONS

Zhang, et al., "High-speed volumetric imaging of cone photoreceptors with adaptive optics spectral-domain optical coherence tomography", Optics Express, May 15, 2006, pp. 4380-4394, vol. 14, No. 10.

* cited by examiner

*Primary Examiner* — James Greece
(74) *Attorney, Agent, or Firm* — Canon USA Inc. IP Division

(57) ABSTRACT

Aberration is measured as phase information at each of a plurality of aberration measurement points, and at the time of correcting the aberration with correction pixels of an aberration correction unit of which the number is greater than the number of the plurality of aberration measurement points, correction pixels corresponding to each aberration measurement point are driven based on the phase information. Regarding correction pixels not positionally corresponding to the aberration measurement points, the aberration correction unit is driven based on phase information in the vicinity of this correction pixel.

10 Claims, 7 Drawing Sheets

ABERRATION CORRECTING METHOD AND ABERRATION CORRECTING APPARATUS

BACKGROUND OF THE INVENTION

1. Field of the Invention

The present invention relates to an aberration correcting method, and an aberration correcting imaging apparatus.

2. Description of the Related Art

Studies are being advanced in the field of adaptive-optics scanning laser ophthalmoscope (AO-SLO) and adaptive-optics optical coherence tomography (AO-OCT), which incorporate adaptive optics (AO) functions in optical systems. Adaptive Optics, as applied to SLO and OCT, refers to techniques used to improve the performance optical systems which adapt to correct aberrations introduced during measuring of an eye. For example, an example of AO-OCT is described in "High-speed volumetric imaging of cone photoreceptors with adaptive optics spectral-domain optical coherence tomography" disclosed by Y. Zhang et al, Optics Express, Vol. 14, No. 10, 15 May 2006. AO-SLO and AO-OCT usually measure a wavefront of the eye using the Shack-Hartmann wavefront sensor. The Shack-Hartmann wavefront sensor method is a method for measuring a wavefront by inputting to be measured light to the eye, and receiving reflected light thereof at a CCD camera through a microlens array. AO-SLO and AO-OCT enable imaging at high resolution by driving a deformable mirror or space phase modulator so as to correct the measured wavefront, and performing imaging of the fundus via these.

In general, when the numerical aperture (NA) of an optical irradiation system is raised to acquire high resolution imaging, an aberration level also increases due to irregularities of optical tissue of the eye, such as the cornea, the crystalline lens, and so forth. Also, the aberration shape is complicated. Although several techniques for correcting this aberration with AO are known, the correction of high levels of aberration and aberration of a complicated shape requires performing aberration measurement at high resolution, and to drive a wavefront correction device at high resolution. A space phase modulator employing liquid crystal enables wavefront correction at such high resolution. A common space phase modulator used for AO can perform correction with resolution of around 600×800 pixels.

On the other hand, the number of lenses in a lens array of the Shack-Hartmann wavefront sensor generally used for AO is around 30×40. Resolution of aberration measurement is determined by this number of lens arrays, and accordingly, there are only 30×40 measurement points.

There are principally two methods to control an aberration corrector by acquiring aberration information from the Shack-Hartmann sensor. One method is to fit aberration to a Zernike polynomial function (Zernike polynomials), and control the aberration corrector according to the coefficients thereof (Zernike coefficients). The other method is to control the aberration corrector based on the wavefront phase at a given aberration measurement point.

In the case of the method of controlling the corrector using Zernike coefficients, the wavefront is expressed by the Zernike polynomial function that yields those coefficients, and accordingly, a control value according to resolution of the corrector can be calculated even when controlling a corrector having different resolution. In the case of the method of controlling the corrector using Zernike coefficients, the wavefront is expressed by the function, and accordingly, when there is disturbance from eyelashes, the eyelid, or the like, at the time of aberration measurement, normal fitting fails, and correction of the wavefront cannot be performed correctly.

On the other hand, in the case of the method of acquiring phase information, correct data can be acquired with regard to the point that the spots on the Shack-Hartmann sensor can be measured. Accordingly, control which is robust regarding disturbance is enabled.

SUMMARY OF THE INVENTION

However, only information at the positions of the aberration measurement points can be acquired as phase information. Accordingly, control has to be performed by correlating a measurement point with a correction point, and in the case that the number of correction points is greater than the number of measured points, the wavefront correction device has not been able to be effectively utilized.

It has been found to be desirable to perform aberration correction with high precision by effectively utilizing a wavefront correction device of which the resolution is higher than the resolution of a wavefront sensor.

According to an embodiment of the present invention, an aberration correcting method includes: measuring, using an aberration measuring unit, an aberration of reflected light acquired by irradiating measurement light on a subject, the aberration being measured as phase information at each of a plurality of aberration measurement points; driving an aberration correction unit to correct pixel values corresponding to each aberration measurement point based on the phase information with correction pixels of which the number is greater than the number of the plurality of aberration measurement points; and driving, regarding correction pixels not positionally corresponding to each of the aberration measurement points, the aberration correction unit based on the phase information in the vicinity of the correction pixel.

Further features of the present invention will become apparent from the following description of exemplary embodiments with reference to the attached drawings.

DESCRIPTION OF THE EMBODIMENTS

The present invention will be described by way of the following embodiments; however, it should be understood that the present invention is by no way restricted to configurations of the following embodiments.

First Embodiment

Description will be made regarding a configuration of a fundus imaging apparatus to which the present invention has been applied as a first embodiment, with reference to FIG. 1.

Description of the present embodiment will be made regarding an example where an eye is the subject of measurement, aberration generated at the eye is corrected by a compensation optical system, and the fundus is imaged. Note that the subject is not restricted to the eye, and may be other tissue such as skin or the like.

Figure 1:
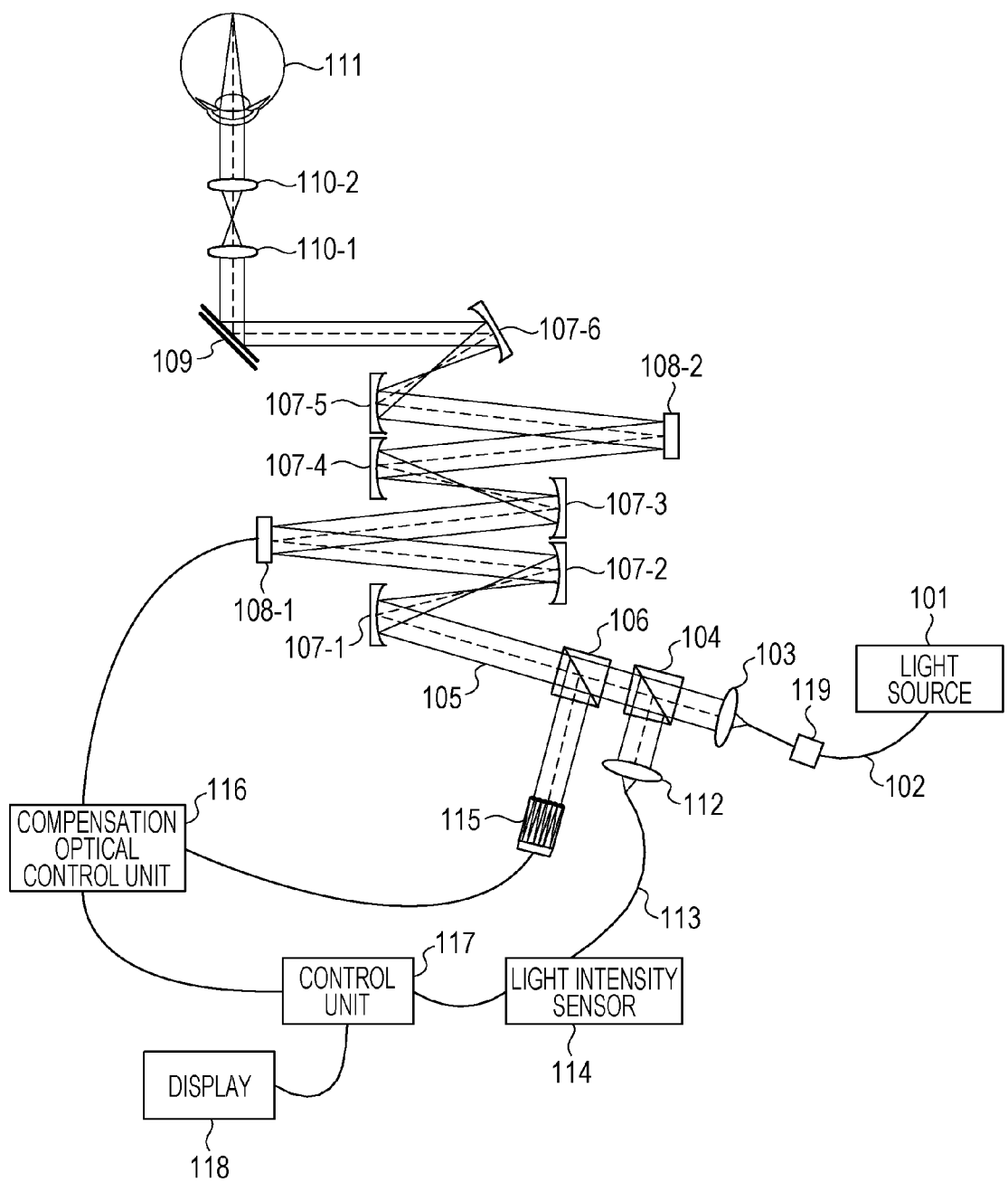
FIG. 1 is a schematic view of a fundus imaging apparatus which uses a scanning laser ophthalmoscope (SLO) including a compensation optical system according to a first embodiment of the present invention.

In FIG. 1, reference numeral 101 denotes a light source. A super luminescent diode (SLD) light source with a wavelength of 840 nm was employed as an example. Though the wavelength of the light source 101 is not restricted to a particular wavelength, a wavelength of around 800 to 1500 nm, for example, is preferably employed for fundus imaging in order to reduce glare of the subject and maintain high resolution. Though an SLD light source has been employed in the present embodiment, a laser or the like may be employed instead. Also, while the configuration of the present embodiment involves the light source being used in common for fundus imaging and for wavefront measuring, an arrangement may be made wherein a separate light source is provided for each of these, and coupled partway along the optical path.

Light irradiated from the light source 101 passes through a single mode optical fiber 102, and is irradiated by a collimator 103 as a parallel light beam (measurement light 105). Polarization of the light to be irradiated is adjusted by a polarization adjustor 119 included on a path of the single mode optical fiber 102. There is another configuration for adjusting the polarization, wherein an optical part configured to adjust the polarization is disposed on the optical path after emission from the collimator 103. The polarization adjustor 119 has been adjusted in the present embodiment so that polarized light emitted from the collimator 103 is a P polarization component. This polarization will be referred to as "first polarization".

The irradiated measurement light 105 transmits through an optical splitting unit 104 including a beam splitter, and is guided to a compensation optical system.

The compensation optical system includes an optical splitting unit 106, a wavefront sensor 115, wavefront correction devices 108-1 and 108-2, and reflecting mirrors 107-1 to 107-6 configured to guide light to the other components.

The reflecting mirrors 107-1, 107-2, 107-3, 107-4, 107-5 and 107-6 are installed so that at least the pupil of an eye 111, wavefront sensor 115, and wavefront correction devices 108-1 and 108-2 have an optical conjugation relationship. Also, a beam splitter is employed in the present embodiment as the optical splitting unit 106. As used herein, the term "beam splitter" is given its genera meaning as understood by a person having ordinary skill in the optical field. Examples of a beam splitter include, but are not limited to, a common cube made of triangular prisms, a half mirror, a half-wave plate, a dichroic mirror or dichroic prism, and polarizing beam splitters, such as a Wollaston prism, among others.

The measurement light 105 which has transmitted through the optical splitting unit 106 is reflected at the reflecting mirrors 107-1 and 107-2 and input to the wavefront correction device 108-1. The measurement light 105 reflected at the wavefront correction device 108-1 is further reflected at the reflecting mirrors 107-3 and 107-4 and input to the wavefront correction device 108-2, and emitted to the reflecting mirror 107-5.

Figure 2:
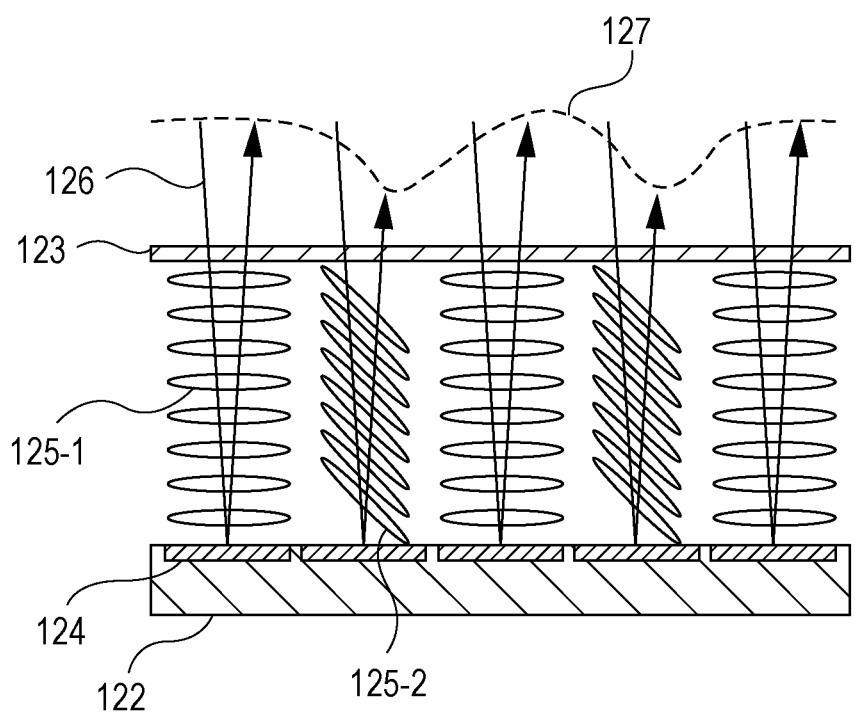
FIG. 2 is a schematic view illustrating an example of a wavefront correction device according to the first embodiment.

Space phase modulators, in which a liquid crystal element is included, are employed as the wavefront correction devices 108-1 and 108-2. Note that a device having fewer correction points than the space phase modulators, such as a deformable mirror, may be employed. That is to say, the wavefront correction devices 108-1 and 108-2 are an example of an aberration correction unit. FIG. 2 illustrates a schematic view of a reflection-type liquid crystal (LC) optical modulator as an example of the space phase modulators in which a liquid crystal element is included. The present modulator has a configuration wherein liquid crystal molecules 125 are sealed in a space between a base portion 122 and a cover 123. The base portion 122 includes a plurality of pixel electrodes 124, and the cover 123 includes transparent counter electrodes which are not illustrated. In a state where no voltage is applied between the electrodes, the liquid crystal molecules 125 have an orientation such as illustrated in FIG. 2 as crystal molecules 125-1. When voltage between the electrodes is applied, the crystal molecules transition to an orientation state such as illustrated as crystal molecules 125-2, and the refractive index as to incident light changes. Spatial phase modulation is therefore enabled by controlling the voltage of each pixel electrode to change the refractive index of each pixel. For example, when incident light 126 is input to the modulator, the phase of the light passing through the liquid crystal molecules 125-2 is delayed as compared to light passing through the liquid crystal molecules 125-1, and consequently, a wavefront such as illustrated by reference numeral 127 in FIG. 2 is formed. The reflection-type liquid crystal optical modulator according to an example of the present embodiment is a modulator having an 800×600 pixel matrix configuration.

The liquid crystal optical modulator such as described above principally modulates light of a certain polarization component.

Accordingly, in order to modulate both polarization components, two wavefront correction devices 108-1 and 108-2, of which polarization components to be modulated are at right angles, are employed in the present embodiment. The wavefront correction device 108-1 modulates first polarization component (e.g., parallel P polarization component), and the wavefront correction device 108-2 modulates a second polarization component (e.g., perpendicular S polarization component), which is at a right angle (orthogonal) to the first polarization component, of the illumination light.

In FIG. 1, light reflected at the reflecting mirrors 107-5 and 107-6 is one-dimensionally or two-dimensionally scanned by a scanning optical system 109. Two galvano scanners are provided to the scanning optical system 109 in the present embodiment as for main scanning (fundus horizontal direction) and for sub scanning (fundus vertical direction). A resonance scanner may also be employed for main scanning of the scanning optical system 109 to realize high-speed imaging. Also, a device configuration may be employed, in which an optical element such as a mirror or lens is disposed between the scanners, in order to change the scanners within the scanning optical system 109 to an optical conjugate state.

The measurement light 105 scanned at the scanning optical system 109 is irradiated on the eye 111 through eyepiece lenses 110-1 and 110-2. The measurement light 105 irradiated on the eye 111 is reflected or scattered at the fundus of the eye. Optimal irradiation conditions can be achieved in accordance with a diopter scale of the eye 111 by adjusting the positions of the eyepiece lenses 110-1 and 110-2. Though the lens system is employed as an example of eyepiece unit in the present embodiment, the eyepiece unit may be configured of a spherical mirror or the like.

The reflected light reflected or scattered from the retina of the eye 111 returns along the same path over which it traveled at the time of entering, part of the returning light is reflected at the wavefront sensor 115 by the optical splitting unit 106. The returning light is used by the wavefront sensor 115 for measuring the wavefront of the light beam. That is to say, the wavefront sensor 115 is an example of an aberration measuring unit configured to measure aberration of reflected light acquired by irradiating measurement light on a subject.

Figure 3A:
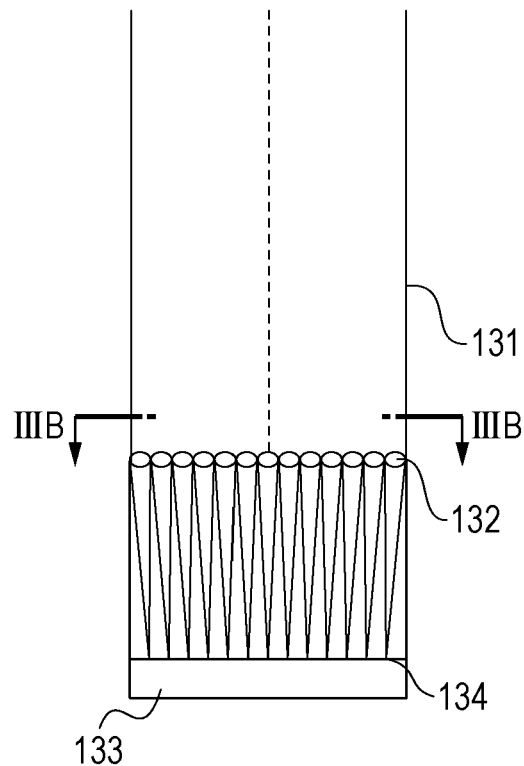
FIGS. 3A and 3B are schematic views illustrating an example of a configuration of a Shack-Hartmann sensor.
Figure 3B:
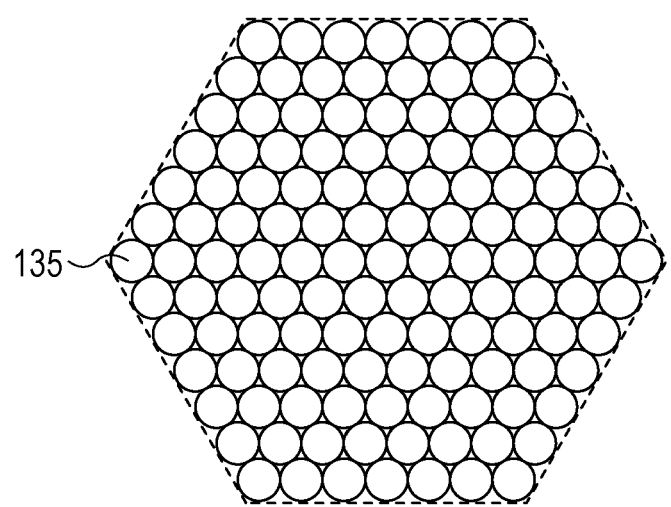
Figure 4:
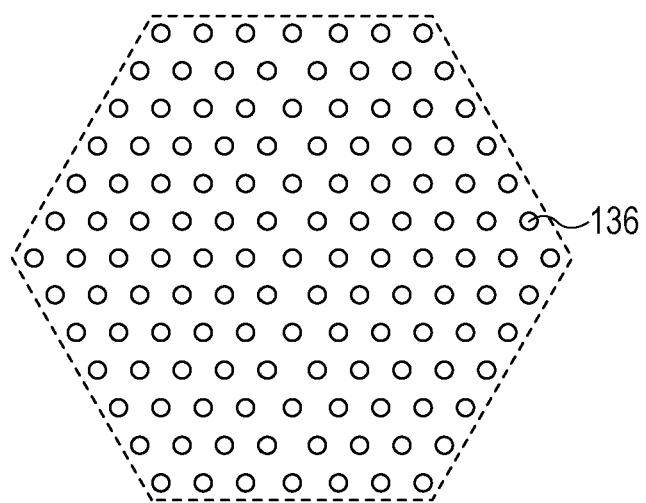
FIG. 4 is a schematic view illustrating an example of a state in which a light beam for measuring a wavefront is condensed on a CCD sensor.

The Shack-Hartmann sensor is employed in the present embodiment as the wavefront sensor 115. FIGS. 3A and 3B illustrate schematic views of the Shack-Hartmann sensor. Reference numeral 131 denotes a light beam of which a wavefront is to be measured. This light beam 131 is condensed on a focal plane 134 on a CCD sensor 133 through a microlens array 132. FIG. 3B is a diagram illustrating the microlens array as viewed from a position indicated by arrows IIIB—IIIB in FIG. 3A. FIG. 3B illustrates the way in which the microlens array 132 is configured of a plurality of microlenses 135. The light beam 131 is condensed on the CCD sensor 133 through each of the microlenses 135, and accordingly, the light beam 131 is condensed by being split into spots of which the number is equivalent to the number of microlenses 135. FIG. 4 illustrates light in a condensed state (focus spots) on the CCD sensor 133. The light beams which have passed through the microlenses 135 are condensed as spots 136. The wavefront of the incident light is calculated from the position of each spot 136 on the surface of the CCD sensor 133. Specifically, each spot 136 on the surface of the CCD sensor 133 represents a measurement point. The gradient of a wavefront at each measurement point is calculated from a difference between an original (or expected) position of each spot and the measured position; this yields an aberration measurement point. Phase information at each aberration measurement point is acquired by integrating the calculated gradient. Also, a Zernike coefficient may also be calculated from difference between each spot original (or expected) position and the actual measured position.

Figure 5A:
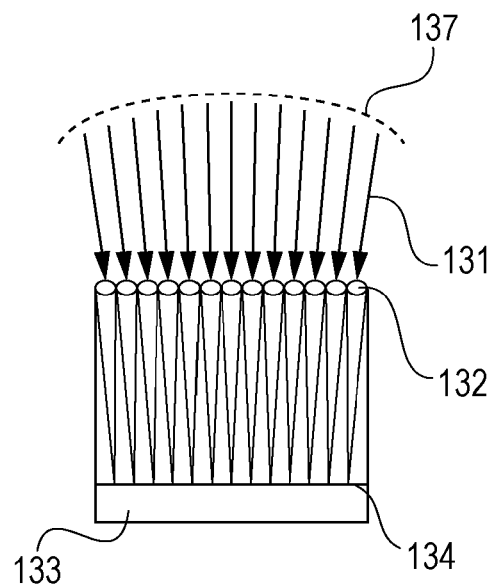
FIGS. 5A and 5B are schematic views illustrating an example at the time of measuring a wavefront having a spherical aberration.
Figure 5B:
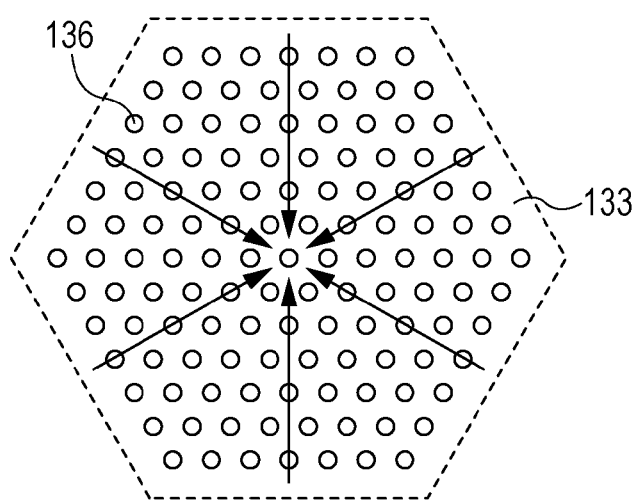

For example, FIGS. 5A and 5B illustrate schematic views in a case where wavefronts having a spherical aberration have been measured. In FIG. 5A, light beams 131 having a wavefront 137 are incident the microlenss array 132. The light beams 131 are condensed locally in the vertical direction of a wavefront by the microlens array 132. The condensed state of the incident light impinging on the CCD sensor 133 in this case is illustrated in FIG. 5B. The light beams 131 have spherical aberration, and accordingly, spots 136 are condensed in a state biased in the center area. The shape of the wavefront formed by the light beams 131 is found by calculating the positions of spots 136 on the CCD sensor 133.

The Shack-Hartmann sensor having a 30×40 microlens array, for example, is employed in the present embodiment. Note that the number of microlenses of the Shack-Hartmann sensor is not restricted to the above value.

In FIG. 1, the reflected light which has transmitted through the optical splitting unit 106 is partially reflected at the optical splitting unit 104, and is guided to a light intensity sensor 114 through a collimator 112 and an optical fiber 113. The light is converted into electric signals at the light intensity sensor 114, and is formed into an image serving as a fundus image by a control unit 117, and the fundus image displayed on a display 118.

The wavefront sensor 115 is connected to a compensation optical control unit 116, and transmits the received wavefront to the compensation optical control unit 116. The wavefront correction devices 108-1 and 108-2 are also connected to the compensation optical control unit 116, and perform modulation instructed from the compensation optical control unit 116. The compensation optical control unit 116 calculates modulation amount (correction amount) for each pixel of the wavefront correction devices 108-1 and 108-2. The correction devices 108-1 and 108-2 correct the wavefront acquired by the CCD sensor, based on measurement results of the wavefront sensor 115 to acquire a wavefront having no aberration. To that end, the compensation optical control unit 116 instructs the wavefront correction devices 108-1 and 108-2 to perform modulation of the light, based on measurement results of the wavefront sensor 115. This wavefront measurement and instruction to the wavefront correction devices is repeatedly (iteratively) processed, and feedback control is performed so as to constantly have an optimal wavefront. Here, the compensation optical control unit 116 is an example of a drive control unit configured to drive an aberration correction unit to correct the wavefront aberration measured by the aberration measuring unit.

A control flow of a process (method) for detecting a fundus image and performing corrections thereof will be described with reference to the flowchart of FIG. 6.

In step S101, the control process is started, and a compensation optical basic flow is executed. The compensation optical basic flow repeatedly performs measurement of aberration using the wavefront sensor 115 to acquire aberration information in steps S102 to S104, calculation of correction amount using the compensation optical control unit 116 based on the measured results in step S106, and driving the correction devices 108-1 and 108-2 based on the control of the compensation optical control unit 116 in step S107.

Specifically, in step S102, the compensation optical control unit 116 measures aberration. This measurement is performed by measuring spots on the Shack-Hartmann sensor, and calculating amount of movement (misalignment amount) from a reference position of the spot position at each measurement point. General amount of movement is represented by displacement amounts in the X-direction and Y-direction. In this example, a 40×30 microlens array Shack-Hartmann sensor is employed to detect the incident light. Accordingly, in a case where measurement light is input to all of the lenses in the array, an amount of movement of spots (aberration) of 40×30=1,200 measurement points is calculated.

In step S103, the compensation optical control unit 116 acquires gradient information of reflected light at each measurement point. The gradient information represents gradients of the wavefront elements. The gradient of a wavefront element is calculated by dividing the amount of movement of the spot by the focal length of the corresponding microlens, which gives the tilt angle of chief ray of the focusing optical beam with respect to the normal of the sensor. The unit of the gradient is expressed in radian. In the same way as with the amount of movement, gradient information at the 1,200 measurement points is acquired. The gradient information in this example is represented by gradient amounts in the X-direction and Y-direction.

In step S104, the compensation optical control unit 116 acquires phase information of reflected light at each measurement point. Specifically, the compensation optical control unit 116 measures aberration as phase information at each of a plurality of aberration measurement points. In the same way as with the gradient information, phase information at the 1,200 measurement points, and aberration amount based on this phase information, is acquired. The phase information is acquired in this example by integrating the gradient information. To reconstruct the phase, gradients of wavefront elements are integrated over the entire measurement points; actual integration is given as grad_x*grad_y dx dy. Also, the aberration amount is acquired as the root mean square of phases at the measurement points. Here, the compensation optical control unit 116 is an example of a phase information acquisition unit configured to acquire phase information at each aberration measurement point. Further, the compensation optical control unit 116 is an example of a gradient acquisition unit configured to acquire gradient information at each aberration measurement point.

Figure 6:
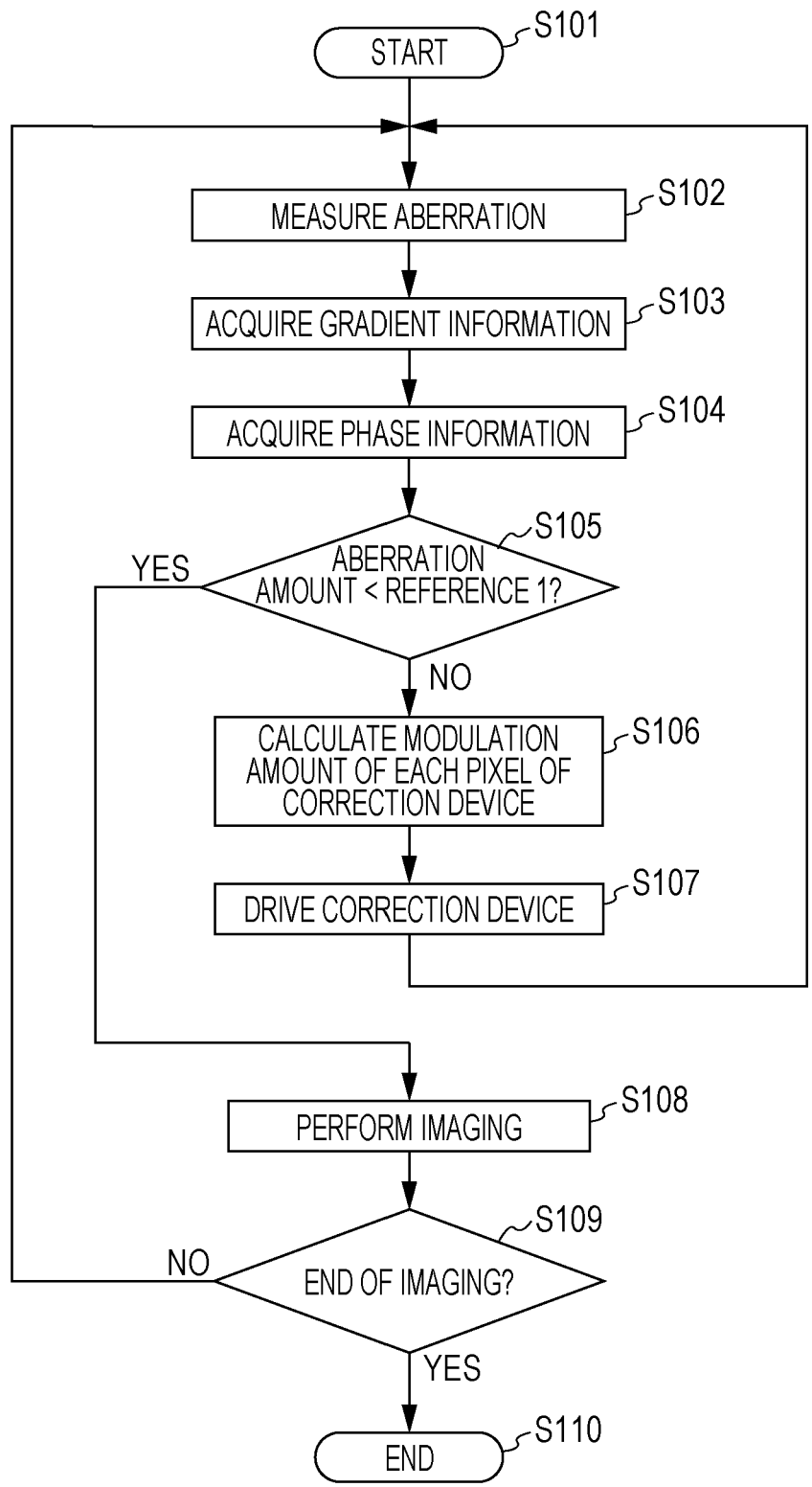
FIG. 6 is a flowchart illustrating an example of a control process of a fundus imaging apparatus according to the first embodiment.

Though not illustrated in FIG. 6, a Zernike coefficient for expressing a wavefront from amount of movement of a measured spot may also be calculated. To that end, the correction devices 108-1 and 108-2 may be controlled based on the Zernike coefficient.

In step S105, whether or not the acquired aberration amount is less than a predetermined reference value (threshold) of aberration amount is confirmed using the compensation optical control unit 116. The aberration amount may be calculated as the root mean square of phases at the measurement points, or the means square of all coefficients in the case of Zernike coefficients having been calculated, though calculation methods differ depending on the method for measuring aberration. Note that even in a case where the reference value has been set beforehand for the device, an operator of the device may set the reference value prior to measurement. In the case that the aberration amount exceeds the reference value of the aberration amount, the processes in step S106 and thereafter are executed. In the case that the aberration amount is less than the reference value of the aberration amount, the flow proceeds to step S108.

In step S106, the correction amount of each pixel of the correction devices is calculated. Here, it should be noted that although the acquired phase information is equivalent to only 1,200 points (based on the Shack-Hartman sensor array), the number of pixels of a space phase modulator to be driven is 480,000 pixels of a 800×600 matrix. Regarding pixels corresponding to the positions of the 1,200 points where phase information has been acquired, the modulation amount of the space phase modulator is decided based on the phase information. Modulation amount may be calculated so as to cancel a phase which is deviation from a reference surface.

Calculation of the modulation amount of a correction point not corresponding to an aberration measurement point is performed using the gradient information. Specifically, the area of the modulator corresponding to each measurement point is calculated. While the number of aberration measurement points is 1,200, the number of correction points is 480,000, and accordingly, in the case that the Shack-Hartmann sensor corresponds to the entire range of the wavefront correction device, 400 pixels of each correction device correspond to one measurement point of the wavefront sensor. The modulation amount of the center pixel (one or several pixels) of the 400 pixels is decided based on the phase information, and proximity within the 400 pixels worth of modulation amount is calculated by adding the gradient information in the X-direction and Y-direction to the center value thereof.

Calculation is performed as follows, for example. In the case that
Center phase value=A,
Gradient sx=amount of movement dx/focal distance f,
Gradient sy=amount of movement dx/focal distance f, and
Pitch of the lens arrays=d,
the modulation amount of coordinates xy (the origin is the coordinates of the center pixel of the 400 pixels) should be calculated so as to correct the following.

$A+((x/200)*d/2*sx)+((y/200)*d/2*sy)$

That is to say, the compensation optical control unit 116 is an example of a drive amount complementing unit configured to calculate drive amount of correction pixels not corresponding to aberration measurement points. Specifically, the drive amount complementing unit calculates drive amount based on the gradient information. The aberration correction unit drives the correction pixels based on the phase information and the calculated drive amount. Driving the correction pixels indicates driving electrodes to rotate the director of liquid crystal and correct wavefront aberrations. That is, correction devices 108-1 and 108-2 are driven to correct wavefront aberrations based on the phase information and the calculated drive amount.

Note that, though the above expression is employed in the present embodiment, this expression is not restrictive, and may be deformed to another expression as long as this is an expression equivalent to the above expression. Also, though the origin of the coordinates xy is taken as the center of the 400 pixels in the present embodiment, the center is not restricted to this, and another position may be taken as the origin. The above expression may also be deformed correspondingly to the position of the origin. Also, the center phase value A indicates the phase value of the origin of the coordinates xy (the position of the light arriving at the CCD sensor 133, for example), and may be acquired by various methods.

As described above, when correcting aberration using correction pixels of the aberration correction unit of which the number is greater than the plurality of aberration measurement points, correction pixels corresponding to each aberration measurement point are driven based on the phase information. On the other hand, the aberration correction unit is driven based on nearby phase information and nearby gradient information regarding correction pixels not positionally corresponding to aberration measurement points as indicated in step S103.

The wavefront correction devices 108 include the first wavefront correction device 108-1 and second correction device 108-2, and accordingly, the step S106 for calculating correction amount has to be performed regarding each of the devices. Also, each of the devices has to be driven regarding the step S107 for driving the device. Thus, the drive amount complementing unit calculates drive amount based on the gradient information, and the aberration correction unit drives the correction pixels based on the phase information and the calculated drive amount.

In the case of having proceeded to step S108, imaging is performed in step S108, and end confirmation is performed in step S109. In the case of having received no end request, compensation optical processes in steps S102 to S107 are performed again, and imaging is performed in step S108. In the case of having confirmed an end request in step S109, the control is ended in step S110.

According to the present embodiment, in the case of employing a wavefront correction device of which the resolution is higher than the resolution of a wavefront sensor, aberration correction with high precision can be performed by effectively utilizing the wavefront correction device. Imaging with high image quality can be realized by performing aberration correction with high precision. Also, in the case of employing a space phase modulator of which the resolution is higher than that of a deformable mirror, the above advantage is even more apparent.

Second Embodiment

Description will be made regarding an example of a fundus imaging apparatus control method according to an embodiment different from the first embodiment to which the present invention has been applied, as a second embodiment, with reference to the flowchart in FIG. 7. The basic device configuration in the present embodiment is the same as with the first embodiment.

In step S201, the control is started, and the compensation optical flow is executed.

In step S202, aberration is measured. This measurement is performed by measuring spots on the Shack-Hartmann sensor, and calculating amount of movement from the reference position of the spot position at each measurement point. The amount of movement is represented by displacement amounts in the X-direction and Y-direction. The 40×30 microlens array Shack-Hartmann sensor is employed in the this example, and accordingly, in the case of measurement light having input to all of the lens arrays, amount of movement at 40×30=1,200 measurement points is calculated.

Next, in step S203, the number of detected spots is confirmed. Though spots corresponding to all of the lens arrays should be detected by light inputting to all of the lens arrays in a normal state, there are spots where detection fails, due to eyelashes, the eyelid, the state within the eyeball such as cataracts, or the like. That is to say, distribution of signal intensity changes due to influence such as eyelashes or the like. The number of the detected spots is compared with a reference 2, which is the number of reference spots optionally specified, and in the case that the number of the spots is greater than the reference 2, correct Zernike coefficients can be calculated from the spots. Accordingly, the flow proceeds to step S206. On the other hand, in the case that the number of the spots is smaller, reliability of the calculable Zernike coefficient is lower, and reliability of the phase information is high, so the flow proceeds to step S204. Let us say that the reference 2 is 1100, which is a value serving as the number of around 90% in this example. That is to say, according to the present embodiment, signal intensity at an aberration measurement point is measured, and whether to perform driving based on the phase information or driving based on the Zernike coefficients is selected in accordance with the signal intensity distribution. Note that calculation of the Zernike coefficients is performed by the compensation optical control unit 116, for example. That is to say, the compensation optical control unit 116 is equivalent to an example of a Zernike coefficient calculating unit configured to measure aberration as a Zernike coefficient.

Now, an arrangement may be made wherein the compensation optical control unit 116 compares the signal intensity with a threshold value, and in the case that the signal intensity is lower than the threshold value, the flow proceeds to step S204, but in the case that the signal intensity is higher than the threshold value, the flow proceeds to step S205. That is to say, the compensation optical control unit 116 is equivalent to an example of a signal intensity discrimination unit configured to compare a signal intensity of a measurement point and an optional threshold value. Next, the compensation optical control unit 116 performs correction of aberration selectively employing the phase information and Zernike coefficients according to the signal intensity.

Steps S204 and S205 are the same as with the first embodiment. The phase information, gradient information, and aberration amount at each measurement point are acquired from the spots.

In step S207, confirmation is made regarding whether or not the aberration amount is less than a predetermined reference value of aberration amount using the compensation optical control unit 116. In the case that the aberration amount exceeds the reference value of the aberration amount, the process in step S210 and thereafter are executed. In the case that the aberration amount is less than the reference value, the flow proceeds to step S212.

In step S210, in the same way as with the first embodiment, modulation amount may be calculated regarding correction points corresponding to aberration measurement points, using the acquired phase information, and modulation amount calculated regarding non-corresponding points based on the phase information and gradient information.

In step S211, the correction device is driven to correct the aberration based on the calculated correction amount of each correction point.

On the other hand, in step S206, coefficients of the Zernike function that express the wavefront of measurement light from the positional information of the spots are calculated.

In step S208, confirmation is made regarding whether or not the aberration amount is less than a predetermined reference value of aberration amount using the compensation optical control unit 116. The aberration amount is calculated as the root mean square of all of the coefficients of the Zernike function. In the case that the aberration amount exceeds the reference value of the aberration amount, the processes in step S209 and thereafter are executed. In the case that the aberration amount is less than the reference value of the aberration amount, the flow proceeds to step S212.

In step S209, in the same way as with processes performed in compensation optical control according to the related art, the modulation amount of all of the correction points is calculated using the Zernike function and the acquired Zernike coefficients.

In step S211, the correction device is driven to correct the aberration based on the calculated correction amount of each correction point. That is to say, the aberration correction unit is driven based on the calculated Zernike coefficients.

After driving the correction device in step S211, the compensation optical flow is executed again by returning to step S202.

In the case of having advanced to step S212, imaging is performed in step S212, and end confirmation is performed in step S213. In the case of having received no end request, compensation optical processes in steps S202 to S211 are performed again, and imaging is performed in step S212. In the case of having confirmed an end request in step S213, the control is ended in step S214.

According to the present embodiment, the same advantage as with the first embodiment can be obtained.

Figure 7:
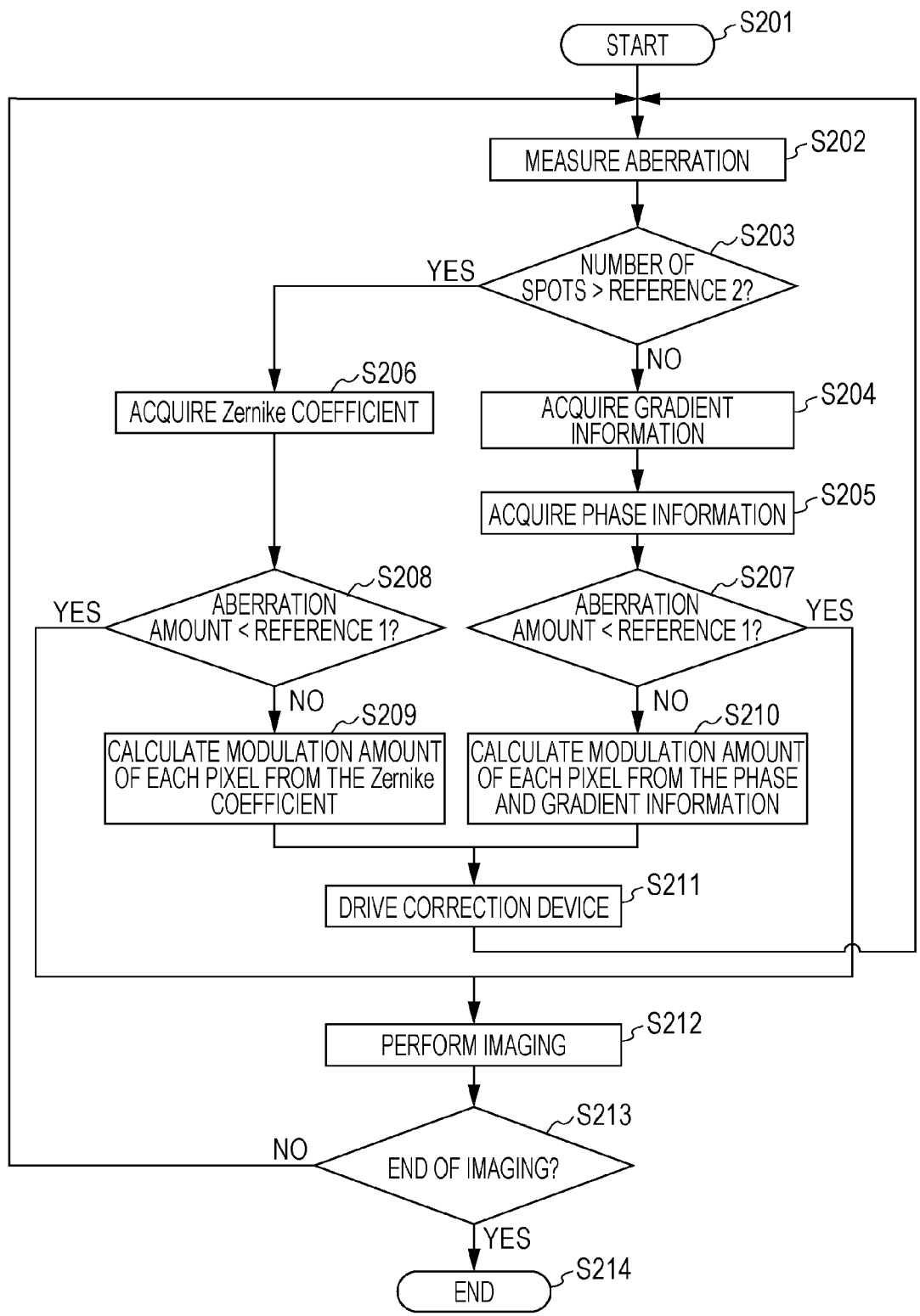
FIG. 7 is a flowchart illustrating an example of control steps of a fundus imaging apparatus according to a second embodiment.

The present embodiment enables selection of whether the correction pixel is to be driven based on the phase information or based on the Zernike coefficients, as illustrated in FIG. 7. That is to say, correction of aberration is performed by selectively employing the phase information and Zernike coefficients. Performing such processing enables optimal compensation optical control to be performed according to the state of the subject, and enables imaging with high image quality in a stable manner under various conditions, even in the case of performing accurate wavefront correction using a space phase modulator.

Note that a wavefront is expressed by a function in the method employing the Zernike coefficients, thereby enabling calculation of a control value according to resolution of the corrector in the case of controlling a corrector having different resolution. However, in the case that there is disturbance, normal fitting fails, and the wavefront is not correctly corrected. Accordingly, in the case that the number of spots is greater than a reference 2, aberration correction employing the Zernike coefficients instead of the phase information is performed. In the case that the number of spots is less than the reference 2, aberration correction employing the phase information is performed to avoid deterioration in precision in the case of aberration correction employing the Zernike coefficients. Thus, aberration correction with high precision can be performed.

Third Embodiment

Description has been made regarding an embodiment in which one reference value and aberration amount are compared in each step in the first and second embodiments.

Description will be made regarding the case of reducing time to arrive at a measurable state in the present embodiment. Specifically, two reference values A and B are provided as reference values to be compared with aberration amount, a plurality of correction pixels corresponding to a measured aberration measurement point are driven with the same correction amount until the aberration amount is less than the reference value A. In the case that the aberration amount has reached the reference 1, control of the first embodiment or second embodiment is implemented using the reference value B. Note that the reference value B is a smaller value than the reference value A.

Time until start of measurement can further be reduced in comparison with the first or second embodiment by performing control in this manner.

OTHER EMBODIMENTS

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-279478, filed Dec. 21, 2012, which is hereby incorporated by reference herein in its entirety.

What is claimed is:

1. An aberration correcting method comprising:
   measuring, using an aberration measuring unit, a wavefront aberration of reflected light acquired by irradiating measurement light on a subject, the wavefront aberration being measured as phase information at each of a plurality of aberration measurement points of the aberration measuring unit;
   measuring, using the aberration measuring unit, wavefront gradient information at each of the aberration measurement points; and
   driving an aberration correction unit having a number of pixels greater than the number of the plurality of aberration measurement points, wherein driving the aberration correction unit comprises:
   driving first pixels of the aberration correction unit positionally corresponding to the aberration measurement points based on the phase information being measured, and
   driving second pixels of the aberration correction unit not positionally corresponding to the aberration measurement points based on (i) the phase information being measured at the aberration measurement points corresponding to each of the first pixels in the vicinity of each of the second pixels, (ii) the gradient information being measured at aberration measurement points corresponding to each of the first pixels in the vicinity of each of the second pixels, and (iii) a distance between each of the first pixels in the vicinity of each of the second pixels and each of the second pixels.

2. The aberration correcting method according to claim 1, further comprising:
   calculating the wavefront aberration as a Zernike coefficient; and
   driving the aberration correction unit based on the Zernike coefficient.

3. The aberration correcting method according to claim 2, further comprising:
   determining whether the aberration correction unit is to be driven,
   wherein whether the aberration correction unit driven is selectable, based on the phase information or based on the Zernike coefficient.

4. The aberration correcting method according to claim 3, further comprising:
   measuring signal intensities of the aberration measurement points; and
   selecting, based on a distribution of the signal intensities, whether to perform driving based on the phase information or driving based on the Zernike coefficient.

5. A non-transient computer-readable storage medium, storing thereon a program for causing a computer to execute the aberration correcting method according to claim 4.

6. An aberration correcting apparatus comprising:
   an aberration measuring unit configured to measure wavefront aberration of the reflected light acquired by irradiating measurement light on a subject, the wavefront aberration being measured as phase information and wavefront gradient information at each of a plurality of aberration measurement points of the aberration measuring unit;
   an aberration correction unit having a number of pixels greater than the number of the plurality of aberration measurement points; and
   a drive control unit configured to drive the aberration correction unit to correct the measured wavefront aberration,
   wherein the drive control unit is configured to drive driving first pixels of the aberration correction unit positionally corresponding to the aberration measurement points based on the phase information being measured, and wherein the drive control unit is configured to drive second pixels of the aberration correction unit not positionally corresponding to the aberration measurement points based on (i) the phase information being measured at the aberration measurement points corresponding to each of the first pixels in the vicinity of each of the second pixels, (ii) the gradient information being measured at aberration measurement points corresponding to each of the first pixels in the vicinity of each of the second pixels, and (iii) a distance between each of the first pixels in the vicinity of each of the second pixels and each of the second pixels.

7. The aberration correcting apparatus according to claim 6,
wherein the aberration measuring unit includes
a phase information acquisition unit configured to acquire the phase information at each aberration measurement point, and
a gradient information acquisition unit configured to acquire the wavefront gradient information at each aberration measurement point;
wherein the drive control unit calculates a drive amount for driving the first pixels based on the gradient information;
and wherein the aberration correction unit drives the first pixels based on the phase information and the calculated drive amount.

8. The aberration correcting apparatus according to claim 7, further comprising:
a Zernike coefficient calculating unit configured to measure the wavefront aberration at the aberration measuring unit as a Zernike coefficient,
where the drive control unit drives the first pixels based on the Zernike coefficient.

9. The aberration correcting apparatus according to claim 6,
wherein the aberration correction unit performs correction of the wavefront aberration selectively using the phase information and the Zernike coefficient.

10. The aberration correcting apparatus according to claim 6,
wherein the aberration measuring unit further includes
a signal intensity discrimination unit configured to compare signal intensities of the measurement points with a threshold value;
and wherein the aberration correction unit performs correction of the wavefront aberration selectively using the phase information and the Zernike coefficient according to the signal intensities.

* * * * *